United States Patent

Hecquet et al.

[11] Patent Number: 6,025,523
[45] Date of Patent: Feb. 15, 2000

[54] PROCESS FOR THE MANUFACTURE OF ACRYLIC ACID FROM ACROLEIN BY A REDOX REACTION AND USE OF A SOLID MIXED OXIDE COMPOSITION AS REDOX SYSTEM IN THE SAID REACTION

[75] Inventors: Gerard Hecquet, Bethune; Jean-Pierre Schirmann, Paris; Michel Simon, Saint-Avold; Charlotte Pham, Saverne, all of France

[73] Assignee: ELF Atochem S.A., Paris-La-Defense, France

[21] Appl. No.: 09/031,700

[22] Filed: Feb. 27, 1998

[30] Foreign Application Priority Data

Feb. 27, 1997 [FR] France ................. 97 02344

[51] Int. Cl.[7] .................................................. C07C 51/16
[52] U.S. Cl. .......................... 562/535; 562/598; 502/113; 502/120; 502/248; 502/306; 502/312; 502/318; 502/321
[58] Field of Search .................... 562/535, 598; 502/113, 120, 248, 306, 312, 318, 321

[56] References Cited

U.S. PATENT DOCUMENTS 3,954,855  5/1976  Wada et al. ................. 260/530 N
5,637,546  6/1997  Tenten et al. ................. 502/312

FOREIGN PATENT DOCUMENTS 43 35 973  4/1995  Germany ................. B01J 23/28

*Primary Examiner*—Rosalynd Keys
*Attorney, Agent, or Firm*—Millen, White, Zelano & Branigan, P.C.

[57] ABSTRACT

Solid mixed oxides composition of formula (I):

$$Mo_{12}V_aSr_bW_cCu_dSi_eO_x \qquad (I)$$

$2 \leq a \leq 14$, $0.1 \leq B \leq 6$, $0 \leq c \leq 12$, $0 \leq d \leq 6$, $0 \leq e \leq 15$; x is the quantity of oxygen bonded to the other elements and depends on their oxidation states, are used in the manufacture of acrylic acid by oxidation of acrolein, the said solid composition reacting with acrolein according to the redox reaction (1):

$$SOLID_{oxidized} + ACROLEIN \rightarrow SOLID_{reduced} + ACRYLIC\ ACID \quad (1).$$

To manufacture acrylic acid, a gaseous mixture of acrolein and of water vapor and, if appropriate, of an inert gas is passed over a solid composition of formula (I), to conduct the redox reaction (1) by operating at a temperature of 200 to 500° C., at a pressure of $1.01 \times 10^4$ to $1.01 \times 10^6$ Pa (0.1 to 10 atmospheres), and with a residence time of 0.01 second to 90 seconds, in the absence of molecular oxygen.

14 Claims, No Drawings

PROCESS FOR THE MANUFACTURE OF ACRYLIC ACID FROM ACROLEIN BY A REDOX REACTION AND USE OF A SOLID MIXED OXIDE COMPOSITION AS REDOX SYSTEM IN THE SAID REACTION

The present invention relates to the manufacture of acrylic acid from acrolein by oxidation according to a redox reaction. The invention also relates to the use of a solid mixed oxides composition as redox system for the said reaction.

BACKGROUND OF THE INVENTION

Industrial production of acrylic acid is at present carried out by vapour phase catalytic oxidation of acrolein. All attempts to improve this process have hitherto related to the development of catalysts giving the highest possible conversion of acrolein and the highest possible selectivity for the desired acrylic acid.

Thus, French Patent No. 2 222 349 describes a catalyst for the preparation of acrylic acid by vapour phase catalytic oxidation of acrolein using a gas containing molecular oxygen, this catalyst including a catalytic oxide on an inert porous support, this catalytic oxide having the following metal composition:

$$Mo_{12}V_{2-14}Z_{0.1-6}W_{0-12}Cu_{0-6}$$

Z being at least one of Be, Mg, Ca, Ba and Sr, and at least one of W and Cu being always present.

This catalyst can be prepared by adding a support (powdered material or α-alumina, silicon carbide or similar beads) to an aqueous solution in which compounds of the various catalyst elements are dissolved, evaporating the aqueous solution to dryness to deposit the catalyst elements on the support and calcining the dried product between 300 and 800° C.

SUMMARY OF THE INVENTION

It has now discovered that acrylic acid can be manufactured by gas phase oxidation of acrolein in the absence of molecular oxygen, by passing a gaseous mixture of acrolein and water vapour and, if appropriate, of an inert gas over a specific solid mixed oxides composition, which acts as a redox system and supplies the oxygen necessary for the reaction.

The advantages of this new process are the following:

the disadvantage of an oxidation with molecular oxygen is the overoxidation promoting the degradation of the products formed; according to the present invention, since the operation is carried out in the absence of molecular oxygen, the formation of $CO_x$ (carbon monoxide and carbon dioxide), degradation products, is reduced, and this allows the selectivity for acrylic acid to be substantially increased;

the selectivity for acrylic acid remains good when the degree of reduction of the solid composition increases;

once it has undergone a reduction and the progressive loss of its activity, the solid composition can be easily regenerated by heating in the presence of oxygen or of a gas containing oxygen after a certain period of use; after the regeneration the solid recovers its initial activity and can be employed in a new reaction cycle;

the separation of the stages of reduction of the solid composition and of its regeneration makes it possible:

to increase the selectivity for acrylic acid; and to increase the partial pressure of acrolein, such a partial pressure of acrolein feed being no longer restricted by the existence of an explosive region of the acrolein+oxygen mixture.

The subject of the present invention is therefore firstly the use of a solid mixed oxides composition of formula (I):

$$Mo_{12}V_aSr_bW_cCu_dSi_eO_x \quad (I)$$

in which:

a is between 2 and 14, limits included, b is between 0.1 and 6, limits included, c is between 0 and 12, limits included, d is between 0 and 6, limits included, e is between 0 and 15, limits included, and x is the quantity of oxygen bonded to the other elements and depends on their oxidation states, in the manufacture of acrylic acid by oxidation of acrolein, the said solid composition reacting with acrolein according to the redox reaction (1):

$$SOLID_{oxidized} + ACROLEIN \rightarrow SOLID_{reduced} + ACRYLIC\ ACID \quad (1).$$

The oxides of the various metals forming part of the composition of the mixed oxide of formula (I) can be employed as raw materials in the preparation of this composition, but the raw materials are not restricted to the oxides; as other raw materials there may be mentioned:

in the case of molybdenum: ammonium molybdate and molybdic acid, in the case of vanadium: ammonium metavanadate, in the case of strontium: strontium hydroxide, carbonate or nitrate, in the case of tungsten: ammonium tungstate and tungstic acid, in the case of copper: copper hydroxide, carbonate or nitrate, and, in general, any compounds capable of forming an oxide on calcination, namely metal salts of organic acids, metal salts of inorganic acids, complex metal compounds and organic metal compounds, and the like.

The source of silicon generally consists of colloidal silica.

In accordance with specific embodiments, solid compositions of formula (I) can be prepared by mixing, with stirring, aqueous solutions of ammonium paratungstate, ammonium metavanadate, ammonium molybdate and copper nitrate and strontium nitrate, adding colloidal silica if appropriate, and then drying them and calcining them in air between 300 and 600° C., preferably between 350 and 500° C.

Another subject of the present invention is a process for the manufacture of acrylic acid from acrolein, according to which process a gaseous mixture of acrolein and of water vapour and, if appropriate, of an inert gas such as nitrogen is passed over a solid composition of formula (I) defined above, to conduct the redox reaction (1) as indicated above, by operating at a temperature of 200 to 500° C., especially from 250 to 450° C., at a pressure of $1.01\times10^4$ to $1.01\times10^6$ Pa (0.1 to 10 atmospheres), especially from $5.05\times10^4$ to $5.05\times10^5$ Pa (0.5–5 atmospheres) and with a residence time of 0.01 second to 90 seconds, especially from 0.1 second to 30 seconds, in the absence of molecular oxygen.

The acrolein/water vapour volume ratio in the gaseous phase is not critical and may vary within wide limits.

During the redox reaction (1), the solid composition undergoes a reduction and a gradual loss of its activity. This is why, once the solid composition has changed to the reduced state, regeneration of the said solid composition is conducted according to the reaction (2):

$$SOLID_{reduced} + O_2 \rightarrow SOLID_{oxidized} \qquad (2)$$

by heating in the presence of an excess of oxygen or of an oxygen-containing gas at a temperature of 250 to 500° C., for the time needed for the reoxidation of the solid composition.

After the regeneration, which can be carried out in temperature and pressure conditions which are identical with or different from those of the redox reaction, the solid composition recovers an initial activity and can be employed in a new reaction cycle.

The redox reaction (1) and the regeneration may be conducted in a two-stage device, namely a reactor and a regenerator which operate simultaneously and in which two charges of solid composition alternate periodically; the redox reaction (1) and the regeneration may also be conducted in the same reactor by alternating the reaction and regeneration periods.

The preparation of acrylic acid according to the invention takes place according to a stoichiometric and noncatalytic reaction.

The following examples illustrate the present invention without, however, restricting its scope. The conversions, selectivities and yields are defined as follows:

$$\text{Conversion (\%)} = \frac{\text{Number of moles of acrolein which have reacted}}{\text{Number of moles of acrolein introduced}} \times 100$$

$$\text{Selectivity (\%) for acrylic acid} = \frac{\text{Number of moles of acrylic acid formed}}{\text{Number of moles of acrolein which have reacted}} \times 100$$

$$\text{Selectivity (\%) for acetic acid} = \frac{\text{Number of moles of acetic acid formed}}{\text{Number of moles of acrolein which have reacted}} \times 100$$

EXAMPLE 1(a)

Preparation of a solid of formula $Mo_{12}V_{4.8}Sr_{0.5}W_{2.4}Cu_{2.2}O_x$, x being the quantity of oxygen bonded to the other elements and depending on their oxidation states.

3.6 g of ammonium paratungstate, 3.0 g of ammonium metavanadate and 12.4 g of ammonium heptamolybdate are introduced into 100 g of water and heated to 100° C. 3.0 g of copper nitrate and 0.62 g of strontium nitrate are introduced into 5 g of water and heated to 100° C. The second solution is added to the first and the resulting solution is then evaporated to dryness and then calcined for 4 hours at 400° C.

EXAMPLE 1(b) (comparative)

Preparation of acrylic acid from acrolein 50 mg of a solid prepared according to Example 1(a) are charged into a tubular reactor and the reactor is then flushed with a continuous flow of 20 ml/minute of air and heated to 300° C. An injection of an aqueous solution of 12% by weight of acrolein, containing $1.1 \times 10^{-6}$ mol of acrolein, is introduced onto the solid. 97% of the acrolein is converted with selectivities for acrylic acid and for acetic acid of 56% and 4% respectively.

EXAMPLE 2

Preparation of acrylic acid from acrolein by a redox reaction.

After the treatment of Example 1(b) the reactor is flushed with a continuous flow of 17 ml/minute of nitrogen and heated to 300° C. An injection of an aqueous solution of 12% by weight of acrolein, containing $1.1 \times 10^{-6}$ mol of acrolein, is introduced onto the solid. 99.1% of the acrolein is converted with selectivities for acrylic acid and for acetic acid of 65% and 6.5% respectively.

EXAMPLE 3

After having conducted the reaction of Example 2 the same solid is again subjected to eleven successive injections of acrolein in the same test conditions as Example 2. The performance values obtained are reported in Table 1. (Injection No. 1 corresponds to Example 2).

TABLE 1

| Injection No. | Acrolein conversion (%) | Selectivity for acrylic acid (%) | Selectivity for acetic acid (%) |
|---|---|---|---|
| 1 | 99.1 | 65 | 6.5 |
| 2 | 98.2 | 79 | 6.5 |
| 3 | 96.5 | 81 | 5.9 |
| 4 | 95.7 | 86 | 5.3 |
| 5 | 92.8 | 89 | 3.9 |
| 6 | 89.8 | 90 | 3.6 |
| 7 | 85.5 | 90 | 3.3 |
| 8 | 83.4 | 92 | 3.1 |
| 9 | 83.9 | 91 | 3.4 |
| 10 | 84.0 | 89 | 3.4 |
| 11 | 73.6 | 90 | 3.6 |
| 12 | 70.8 | 91 | 3.6 |

EXAMPLE 4

After the reducing treatment of Example 3 the solid is regenerated for 2 hours at 300° C. under a flow of air and then placed back under a flow of nitrogen. Twenty-four new successive injections of aqueous solution of 12% by weight of acrolein, containing $1.1 \times 10^{-6}$ mol of acrolein, are introduced onto the solid.

The performance values obtained are reported in

TABLE 2

| Injection No. | Acrolein conversion (%) | Selectivity for acrylic acid (%) | Selectivity for acetic acid (%) |
|---|---|---|---|
| 1 | 99.5 | 61 | 5.3 |
| 2 | 90.8 | 79 | 3.8 |
| 3 | 97.7 | 84 | 5.3 |
| 4 | 94.2 | 90 | 4.0 |
| 5 | 93.0 | 88 | 3.8 |
| 6 | 91.4 | 89 | 3.5 |
| 7 | 83.2 | 91 | 2.9 |
| 8 | 82.3 | 90 | 3.0 |
| 9 | 82.4 | 90 | 3.3 |
| 10 | 78.6 | 90 | 3.4 |
| 11 | 71.4 | 91 | 3.6 |
| 12 | 68.5 | 89 | 3.8 |
| 13 | 67.8 | 90 | 3.7 |
| 14 | 62.5 | 90 | 3.7 |
| 15 | 61.5 | 89 | 3.7 |
| 16 | 58.1 | 90 | 3.8 |
| 17 | 56.2 | 92 | 3.8 |
| 18 | 54.7 | 91 | 3.7 |
| 19 | 54.1 | 91 | 3.7 |
| 20 | 49.1 | 92 | 3.9 |
| 21 | 47.5 | 92 | 3.9 |

TABLE 2-continued

| Injection No. | Acrolein conversion (%) | Selectivity for acrylic acid (%) | Selectivity for acetic acid (%) |
|---|---|---|---|
| 22 | 49.1 | 92 | 3.7 |
| 23 | 47.8 | 93 | 3.7 |
| 24 | 42.6 | 94 | 3.9 |

The preceding examples can be repeated with similar success by substituting the generically or specifically described reactants and/or operating conditions of this invention for those used in the preceding examples.

The entire disclosure of all applications, patents and publications, cited above and below, and of corresponding French application No. 97/02344, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

As for the expression "in the substantial absence of molecular oxygen" in the claims, it is to be understood that the greater the removal of oxygen from the reactor prior to the reaction, the better the selectivity to acrylic acid will be. However, a chemical engineer will readily recognize that the extent of removal of molecular oxygen is a cost/benefit problem. For example, it might be very expensive to remove final traces of molecular oxygen to obtain only a slight improvement. Thus, the word "substantial" is intended to convey an absence of molecular oxygen which leads to an improved result as compared to a process where no effort is made to eliminate molecular oxygen, for example those processes set forth in the comparative examples.

We claim:

1. A process for the manufacture of acrylic acid from acrolein, according to the redox reaction (1):

$$\text{SOLID}_{oxidized} + \text{ACROLEIN} \rightarrow \text{SOLID}_{reduced} + \text{ACRYLIC ACID} \quad (1),$$

said process comprising passing a gaseous mixture of acrolein and of water vapour and optionally of an inert gas over a solid composition of formula (I):

$$\text{Mo}_{12}\text{V}_a\text{Sr}_b\text{W}_c\text{Cu}_d\text{Si}_e\text{O}_x \quad (I)$$

in which:
 a is between 2 and 14,inclusive,
 b is between 0.1 and 6,inclusive,
 c is between 0 and 12,inclusive,
 d is between 0 and 6,inclusive,
 e is between 0 and 15,inclusive,
 x is the quanity of oxygen bonded to the other elements and depends on their oxidation state, the said solid composition reacting with the acrolein at a temperature of 200 to 500° C., at a pressure of $1.01 \times 10^4$ to $1.01 \times 10^6$ Pa (0.1 to 10 atmospheres) and with a residence time of 0.01 second to 90 seconds, in the substantial absence of molecular oxygen.

2. A process according to claim 1, wherein the redox reaction (1) is conducted at a temperature of 250 to 450° C.

3. A process according to claim 1, wherein the redox reaction (1) is conducted at a pressure of $5.05 \times 10^4 – 5.05 \times 10^5$ Pa (0.5–5 atmospheres).

4. A process according to claim 2, wherein the redox reaction (1) is conducted at a pressure of $5.05 \times 10^4 – 5.05 \times 10^5$ Pa (0.5–5 atmospheres).

5. A process according to claim 1, wherein the redox reaction (1) is conducted with a residence time of 0.1 second to 30 seconds.

6. A process according to claim 4, wherein the redox reaction (1) is conducted with a residence time of 0.1 second to 30 seconds.

7. A process according to claim 1, wherein once the solid composition is converted to the reduced state, said solid composition is regenerated according to the reaction (2):

$$\text{SOLID}_{reduced} + \text{O2} \rightarrow \text{SOLID}_{oxidized} \quad (2)$$

by heating in the presence of an excess of oxygen or of an oxygen-containing gas at a temperature of 250 to 500° C, for the time needed for the reoxidation of the solid composition.

8. A process according to claim 7, wherein the redox reaction (1) and the regeneration are conducted in a two-stage device comprising a reactor and a regenerator which operate simultaneously and in which two charges of solid composition alternate periodically.

9. A process according to claim 7, wherein the redox reaction (1) and the regeneration are conducted in the same reactor by alternating the reaction and regeneration periods.

10. A process according to claim 1 further comprising prior to the reaction, introducing the solid composition into a reactor and flushing the resultant reactor with a continuous flow of an inert gas to remove molecular oxygen.

11. A process according to claim 10, wherein the reaction is conducted in the absence of molecular oxygen.

12. A process according to claim 1 further comprising heating the solid composition to 200–500° C. and introducing an aqueous solution of acrolein over the solid composition to initiate the reaction.

13. A process according to claim 10 further comprising heating the solid composition to 200–500° C. and introducing an aqueous solution of acrolein over the solid composition to initiate the reaction.

14. A process according to claim 1, wherein the solid composition is of the formula $$\text{Mo}_{12}\text{V}_{4.8}\text{Sr}_{0.5}\text{W}_{2.4}\text{Cu}_{2.2}\text{Ox}.$$

* * * * *